United States Patent [19]

Sturm

[11] 4,155,936
[45] May 22, 1979

[54] PARA-NITRODIPHENYLAMINES SYNTHESIS USING POLYETHERS AND MACROCYCLIC ESTERS AS SOLUBILIZING AGENTS

[75] Inventor: Budd H. Sturm, Hartville, Ohio

[73] Assignee: The Goodyear Tire & Rubber Company, Akron, Ohio

[21] Appl. No.: 884,502

[22] Filed: Mar. 8, 1978

[51] Int. Cl.$^2$ ............................................. C07C 85/04
[52] U.S. Cl. .................................... 260/576; 260/571; 260/582
[58] Field of Search ....................... 260/576, 582, 571

[56] References Cited

FOREIGN PATENT DOCUMENTS 844851 6/1965 Belgium.
2534851 2/1977 Fed. Rep. of Germany ............ 260/453

OTHER PUBLICATIONS

Dye et al., "J. Amer. Chem. Soc.", vol. 92(17), pp. 5226-5228 (1970).

Dewald et al., "The J. Phys. Chem.", vol. 68(1), pp. 121-127 (1964).

Schwuger, "Chem. Ab.", vol. 78, Ab. No. 45399p, (1973).

Primary Examiner—Winston A. Douglas
Assistant Examiner—John Doll
Attorney, Agent, or Firm—D. B. Little

[57] ABSTRACT

Processes for synthesizing para-nitrodiphenylamines whereby a para-halonitrobenzene is reacted with an aromatic amine selected from the group consisting of formanilides and anilines (substituted and unsubstituted) in the presence of a basic material (to remove acid) are improved by the incorporation of certain select solubilizing agents into the reaction medium. These solubilizing agents are linear, branched, or cyclic polyethers. Some of the resulting advantages are: higher reaction yield, less by-products, and a faster reaction.

11 Claims, No Drawings

PARA-NITRODIPHENYLAMINES SYNTHESIS USING POLYETHERS AND MACROCYCLIC ESTERS AS SOLUBILIZING AGENTS

BACKGROUND OF THE INVENTION

The field of this invention is carbocyclic amines. More particularly, this invention relates to an improvement in the known processes for making para-nitrodiphenylamines.

Para-nitrodiphenylamines are useful intermediates in the formation of rubber antioxidants and antiozonants. Their generic formula is as follows:

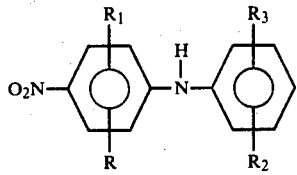
(I)

R and $R^1$ are selected from the group consisting of hydrogen and alkyl radicals (1-9C). $R_2$ and $R_3$ are selected from the group consisting of hydrogen, alkyl radicals containing from 1 to 9 carbon atoms (1-9C), alkoxy radicals 1-9C and cycloalkyl radicals 5-6C.

These compounds are synthesized by reacting: (1) para-halonitrobenzenes conforming to the following structural formula:

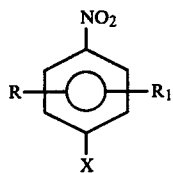
(II)

wherein X is a halogen selected from the group consisting of chlorine and bromine; (2) with a primary aromatic amine of the following structural formula:

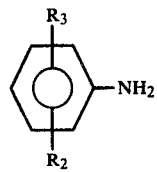
(III)

(3) in the presence of a neutralizing agent (which neutralizes the acid formed and which is usually charged in a slight excess, 2-12%, over theoretical amount) selected from the group consisting of alkali metal salts, oxides of alkali metals, and alkali metal hydroxides; (4) in the presence of copper or a copper salt catalyst (e.g. cuprous cyanide) at a concentration of at least 0.1 parts by weight per 100 parts by weight of the para-halonitrobenzene; (5) at a temperature of 170° to 215° C.; (6) at a pressure of from atmospheric to about 300 kPa (kilopascals); and (7) with an excess of primary aromatic amine of from 5 to 300%. A preferred pressure is about atmospheric pressure.

There is an alternative process to the above catalytic process for making para-nitrodiphenyl amines which is called the formanilide process, which is similar to the above catalytic process except for the following: (1) there is no catalyst; (2) instead of a primary aromatic amine, the second reactant is a formanilide of the following structural formula:

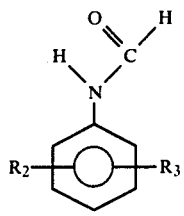
(IV)

(3) the temperature range of the reaction is from 120° to 195° C.; and (4) there is from 0 to 100% excess formanilide over the amount theoretically necessary to react with the para-halonitrobenzene.

The catalytic process is described in British Pat. Nos. 798,148; 834,510; German Pat. No. 185,663 and U.S. Pat. No. 3,155,727. The reaction which occurs is believed to be,

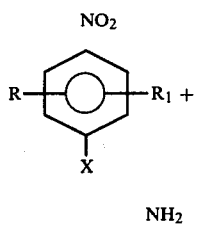
(V)

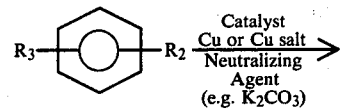

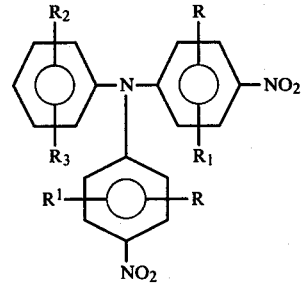

Impurities, such as

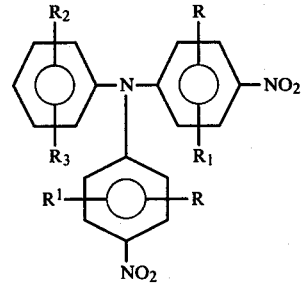
(VI)

(4,4'-dinitrotriphenylamines) are also formed in small amounts.

An example of the neutralizing process is, $HX + K_2CO_3 \rightleftarrows KHCO_3 + KX$     VII $2KHCO_3 \rightarrow H_2O + CO_2 \uparrow + K_2CO_3$     VIII This step serves the important function of removing the acid (HX) which can impede the main nucleophilic substitution reaction.

The formanilide process is described in German Pat. No. 1,056,619 and is believed to proceed by the following reaction:

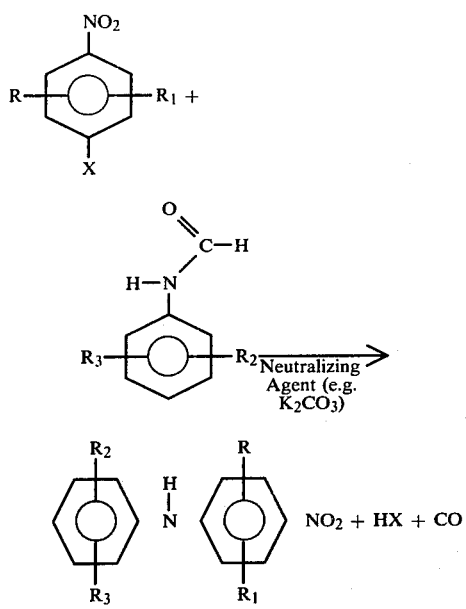

The neutralization of the HX is the same as reactions VII and VIII above.

A moderately good yield of para-nitrodiphenylamine (75–90%) can be obtained by the catalytic process; but the reaction times are somewhat long (10–24 hours). The best yield are obtained at temperatures lower than 205° C. and at times in excess of 12 hours. The product quality suffers by having a fair amount of tars and by-products in the final product. The work-up or purification of this product is faster than in the formanilide process, and the COD level of the wastewater stream resulting from this work-up is generally less than that resulting from the work-up of the formanilide process.

The use of formanilide in the catalytic process woth CuO catalyst is found in U.S. Pat. No. 3,313,854.

In the work-up after the catalytic process reaction is complete, the reaction mixture is cooled to below about 100° C., and water and an organic liquid which azeotropes with water are added to the reaction mixture. The amount of water added is sufficient to dissolve the inorganic salts present. The azeotroping organic liquid is added in sufficient quantity to facilitate a rapid separation of the aqueous and organic phase. The resulting mixture is agitated at an elevated temperature (e.g. approximately 85° C.) for a time sufficient to transfer most of the inorganic salts to the water phase. The agitation is stopped, and the aqueous and organic phases are permitted to separate. The aqueous phase containing inorganic salt ions (e.g. cuprous, cyanide, potassium, chloride and carbonate), the azeotroping organic liquid (e.g. toluene or benzene), aniline, and some para-chloronitrobenzene, flows to effluent treatment. This water wash and decant step is followed by an azeotropic distillation. After this azeotropic drying step, the last traces of inorganic salts come out of solution, and they can be removed by filtration of the hot organic phase.

On the other hand, the work-up of the formanilide process involves the steps of: (1) cooling the mixture below about 100° C.; (2) adding an organic liquid which forms a minimum boiling azeotrope with water; (3) adding water and an hydrolysis catalyst (e.g. 15% NaOH); (4) agitating the resulting mixture at an elevated temperature (e.g. approximately 95° C.) for a time sufficient to hydrolize the excess formanilide remaining (e.g. 1½ hours); (5) stopping the agitation and permitting the aqueous and organic phases to separate; and (6) decanting the aqueous layer, containing inorganic salts (e.g. KCl, NaOH and unreacted $K_2CO_3$), alkali metal formates (e.g. potassium and sodium formate), aniline, para-chloronitrobenzene, formanilide, and some of the azeotroping organic liquid. This decanted aqueous phase flows to effluent treatment. It is higher in COD than the corresponding stream from the catalytic process, principally because formates and formanilide contained therein are much more soluble in water than aniline (the main organic in the catalytic process effluent stream). Most of the aniline obtained from the hydrolysis remains in the organic phase and may be recovered by distillation later in the process.

The above procedure can be followed by a hot water wash. This consists of adding water to the organic phase and agitating the two phases at an elevated temperature (85°–90° C.) and thereafter decanting the two phases to remove any residual inorganic salts and unhydrolyzed formanilide in the water phase which is sent to effluent treatment.

The formanilide process reaction normally takes from 4 to 9 hours with a product yield of from about 85 to 98%. The best yields are obtained at the lower temperatures, but require the longest times. However, the hydrolysis reaction in the work-up at the end of the reaction is time consuming and reduces the time advantage that the formanilide process has over the catalytic process.

The following patents represent efforts to use polar solvents as an aid in the synthesis of nitrodiphenylamines: U.S. Pat. No. 3,053,896 (water); U.S. Pat. No. 3,055,940 (dimethylformamide (DMF) and hexamethylphosphoramide); U.S. Pat. No. 3,121,736 (tetrasodium salt of ethylenediaminetetraacetic acid (EDTA), autoclave conditions, 24 hours, 210° C., 80% yield); U.S. Pat. No. 3,277,175 (dimethylsulfoxide); British Pat. No. 839,420 (DMF and hexamethyl phosphoramide); British Pat. No. 850,870 (salicylates and methylsalicylamide); British Pat. No. 877,884 (water and 60 atmospheres pressure); and Belgian Pat. No. 618,462 (DMF).

Several of the foregoing patents disclose the use of DMF in the reaction. There are certain problems involved with the use of DMF which are: (1) DMF boils at 153° C. and distills with the volatiles (e.g., aniline, water and toluene) in the reaction mixture into the reflux column and condenser with which the reactor is normally fitted. It is thereafter necessary to recycle the DMF back to the reactor from an overhead receiver. This condition makes constant monitoring of the volatiles necessary to ensure ideal reaction conditions. (2) DMF is readily absorbed through the skin and can carry impurities with it. The health hazards connected with handling primary aromatic amines (e.g. aniline) and such compound as cuprous cycanide in DMF are manifest.

There is also a problem connected with the presence of water in the system. As can be seen from reaction VIII, the presence of water in sufficient quantity will greatly retard the reaction. That is why the reactor is normally fitted with a refluxing apparatus. The water can be removed by boiling it off. This "drying" is aided by the presence of the azeotroping organic liquid.

Japanese Patent Publication No. 70/09452 discloses the use of diethylformamide and cupric iodide as a catalyst system in a catalytic type process.

Netherlands application No. 65/06527 (Nov. 23, 1965) discloses the use of amides (e.g. acetanilide) in a catalytic type process.

Belgian Pat. No. 844,851 describes the solubilization of alkali metal salts in organic solvents by the use of polyethylene glycol ethers having the formula

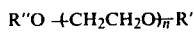

in which n is 6 or more, and R" and R' are alkyl, aryl or cycloalkyl. This patent also discusses the use of macrocyclic polyethers having about 4–20 oxygen atoms, each being separated by two carbon atoms as solubilizing agents for inorganic salts. The above solubilizing agents are described in the Belgian patent as useful in catalyzing substitution reactions.

The present invention is a solution to the problem of long reaction times which avoids the disadvantages inherent in the use of DMF or water, and at the same time it results in higher yields and fewer by-products.

SUMMARY OF THE INVENTION

The benefits mentioned in the paragraph above are achieved by a process improvement which can be utilized in either the catalytic or the formanilide process, which improvement comprises incorporating into the reacting mixture:

(1) a solubilizing agent selected from the group consisting of:
  (a) macrocyclic ethers;
  (b) polyethers having as a major part of their structure the moiety

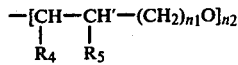

wherein $R_4$ is selected from the group consisting of methyl and hydrogen, $R_5$ is selected from the group consisting of —H and —OH, $n_1$ is 0 or 1, $n_2$ is equal to or greater than 1; and
  (c) compounds having structures selected from the structures of the macrocyclic ethers of (a) and the polyethers of (b) wherein the oxygen in ether linkages has been replaced with a moiety selected from the group consisting of nitrogen and sulfur;

(2) in a concentration of from 0.01 to 50 parts by weight of solubilizing agent per 100 parts by weight para-halonitrobenzene.

Representative of the polyethers of (1) (b) above are the following:

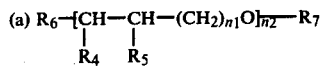 (X)

wherein $R^6$ is selected from the group consisting of hydrogen, hydroxy, alkyl (1–30 C), alkyloxy (1–30 C), alkyl phenoxy (1–30 C), phenoxy and acetoxy, and wherein $R^7$ is selected from the group consisting of hydrogen, alkyl (1–30 C), alkyl phenyl (1–30 C) and phenyl;
(b) adducts of two or more polyethers having the formula of (a) above with each other;
(c) adducts of one or more polyether having the formula of (a) above wherein $R_5$ is hydrogen, either $R_6$ or $R_7$ is an hydroxy group, and $n_1$ is 0 with a compound selected from the group consisting of
  ($c_1$) aliphatic, benzyl, cycloaliphatic and alkenyl alcohols (1–30 C), ($c_2$) aliphatic amines (1–30 C), ($c_3$) aliphatic polyamines (1–30 C), with the proviso that the amine and polyamine adducts are tertiary amines, ($c_4$) salts of alkylaryl sulfonates, and ($c_5$) salts of polyalkoxyalcohol esters of sulfosuccinic acid;
(d) alkylamine guanidine polyoxyalcohols;
(e) polyoxyalkyl esters of organic acids; and
(f) branched polyether with the repeating moiety

and end groups selected from the group $R_6$ and $R_7$.

In general the solubilizing agents of this invention are non-volatile and do not distill with the reactor overheads during the reaction, unlike DMF.

The improved results achieved by this process improvement in the catalytic process are:

(1) faster reaction time (cut by a factor of 3 to 4 in some cases);
(2) improved yield;
(3) a decrease in the copper salt ion concentrations in the effluent stream from the work-up in some cases;
(4) simplification of the work-up from the three step process described in the background section to a one step physical separation (e.g. centrifuge or filter); and
(5) in the normal work-up, a better water phase separation in the water wash step.

Without the solubilizing agents the impurities or tars present at the end of the reaction attach themselves to the inorganic salts (e.g. KCl) present, thus making physical separation techniques very difficult. However, the solubilizing agents employed in this invention act as detergents cutting the tars from the inorganic salts, thus alleviating the need to form a separate water phase into which the inorganics are extracted. It is possible to remove the salts by filtering the reaction product directly. Even in the normal work-up the filter cake is granular and free of organics after a simple toluene cake wash; whereas, in the absence of the solubilizing agent the cake is sticky and tarry.

The advantages realized in the formanilide process are:

(1) faster reaction times (cut in half in some cases);
(2) a possible reduction in the concentration of formanilide charged without losing quality and yield of para-nitrodiphenylamines; and
(3) a possible reduction in the COD of the effluent from the work-up as a result of reducing the formanilide charge.

DESCRIPTION OF THE PREFERRED EMBODIMENTS

The preferred solubilizing agents are the polyethers, wherein $R_4$ and $R_5$ are hydrogen and $n_1$ is O. Of these compounds, the more preferred are polyethylene glycols and alkoxy terminated polyethylene glycols, e.g. methoxy terminated polyethylene glycols.

Solubilizing agents with long chain polyether moieties are preferred; however, as molecular weight increases over about 20,000 viscosity of the reacting mixture can become a problem (undo amounts of energy spent in agitation). The benefits of higher molecular weight are: (1) a further lowering of copper salt ion concentration in effluent water and (2) easier handling characteristics (less waxy than low molecular weight polyethers).

The relatively low molecular weight solubilizing agents which fit the definition given in the summary (e.g. macrocyclic ethers and short chain polyethylene glycols) have the advantage that they can possibly be reused. After the reaction, they can be stripped out and recycled; whereas, the other solubilizing agents are not volatile enough to permit this.

For a given solubilizing agent, increasing concentration increases reaction rate up to a point. This point is about 4–6 parts by weight per 100 parts by weight of para-chloronitrobenzene (PCNB) in the case of the linear polyethers and about one to two parts by weight per 100 parts PCNB in the case of the macrocyclic polyethers. Also, as concentration of the solubilizing agent increases, reaction yield may decrease.

It is postulated that the solubilizing agents of this invention work by loosely coordinating the alkali metal cation of the neutralizing agent. The solubilizing agents are illustrated by the following list:

1. Diethylene glycol monomethylether $CH_3$—O—$CH_2$—$CH_2$—O—$CH_2$—$CH_2$—OH (Methyl Carbitol®)
2. Diethylene glycol — (HO—$CH_2$—$CH_2)_2$O
3. Triethylene glycol diacetate $CH_3CO(OC_2H_4)_3 OCOCH_3$
4. Tetraethylene glycol —HO—$(CH_2CH_2O)_4$H
5. Triethylene glycol dimethylether $CH_3O(CH_2$—$CH_2$—O$)_3CH_3$
6. Ethylene glycol monoethyl ether $C_2H_5$—O—$CH_2$—$CH_2$—OH
7.

$C_9H_{19}$—⟨⟩—O—$(CH_2CH_2$—O$)_{\overline{n_2}}$—H, $n_2 = 1$ or 2, sold as Igepal® CO-210
8. Same as 7 except $n_2=4$, sold as Igepal® CO-430 surfactant
9. Same as 7 except $n_2=6$, sold as Igepal® CO-530 surfactant
10. Same as 7 except $n_2=9$, sold as Igepal® CO-630 surfactant
11. Same as 7 except $n_2=100$, sold as Igepal® CO-990 surfactant
12. 30% $H_2O$. 70% surfactant, $C_8H_{17}$—⟨⟩—O—$(CH_2$—$CH_2$—O$)_{\overline{n_2}}$—H, where $n_2=40$, sold as Igepal® CA-897 surfactant
13.

$C_8H_{17}$—⟨⟩—O—$(CH_2$—$CH_2$—O$)_{\overline{n_2}}$—H, where $n_2=40$, sold as Igepal® CA-890 surfactant 14. Dialkyl ⟨⟩—⟨⟩—O—$(CH_2$—$CH_2$—O$)_{\overline{n_2}}$H, where $n_2$ = approximately 30, sold as Igepal® DM-880
15. Dibenzo-18-crown-6 ether where ⧸\ represents $\begin{matrix} H_2 & H_2 \\ C-C \end{matrix}$ 16. Benzo-15-crown-5 ether 17. 18-Crown-6 ether 18. 15-Crown-5 ether 19. Acrylic emulsion containing alkylpolyether alcohols, 50% concentrations, sold as Triton®-B
20. Z—N—$CH_2$—$CH_2$—N—Z, where Z is:

$[H(-O-CH_2-CH_2)_{\overline{n_2}}(O-CH_2-\overset{CH_3}{\overset{|}{CH}}-)_{n_2'}]_{\overline{z}}$ 80 mole %     20 mole % approximate MW (molecular weight) 3500–4000, sold as Tetronic®-908 surfactant
21.

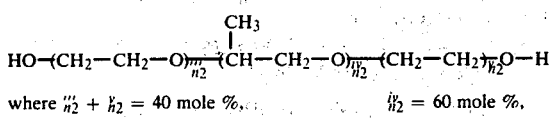

where $m_2 + h_2 = 40$ mole %, $h_2 = 60$ mole %.

approximate molecular weight (MW) of 1750 sold as Pluronic④L-64 surfactant
22. High MW polyethoxylate rosin amine sold as Witconol RAD⑤-1110
23. Propoxylated glycerol, approximate MW of 3000, sold as Witconol⑤CC-43
24. 12 Moles of ethylene oxide on tridecyl alcohol, sold as Witconol⑤SM-120
25. Polyethylene glycol approximate MW 380–420, sold as Carbowax①-400
26. Polyetheylene glycol approximate MW 3000–3700, sold as Carbowax①-4000
27. Polyethylene glycol approximate MW 6000–7500, sold as Carbowax①-6000
28. Polyethylene glycol linearpolymer about MW 15,000, obtained as polyethylene glycol compound 20M from Union Carbide Corporation
29. Partially branched polyethylene glycol approximate MW 15,000 obtained as polyethylene glycol compound 20M - partially branched polymer from Union Carbide Corp.
30. Polyethylene glycol, about 12,500–15,000 MW, sold as Carbowax①-14,000
31. Linear polyethylene oxide, approximate MW 400,000 sold as Polyox①WSR-N-3000
32. Partially branched polyethylene oxide polymer, approximately 600,000 MW, sold as Polyox①WSR-205
33. Partially branched polyethylene oxide polymer, approximately 4,000,000 MW, sold as Polyox①WSR-301
34. Ethylene oxide adduct to ethylene diamine to give mixed amine product, sold as Amine 170⑥
35. $(HO-CH_2-CH_2)_2$ $N-CH_2-CH_2-N-(C-H_2-CH_2-OH)_2$ sold as Amine 120⑥
36. Methoxy capped polyethylene glycol polymer, approximately MW 335–365, sold as Carbowax①Methoxy Polyethylene Glycol 350.
37. Methoxy capped polyethylene glycol polymer, approximately MW 525–575, sold as Carbowax①Methoxy Polyethylene Glycol 550
38. Methoxy capped polyethylene glycol polymer approximately 715–785 MW, sold as Carbowax①Methoxy Polyethylene Glycol 750
39. Methoxy capped polyethylene glycol polymer, approximately 1900 MW, sold as Carbowax①Methoxy Polyethylene Glycol - 2000
40. Methoxy polyethylene glycol polymer, approximately 5000 MW, sold as Carbowax①Methoxy Polyethylene Glycol - 5000

①— A Trademark of Union Carbide Corportion.
②— A Trademark of GAF Corporation
③— A Trademark of Rohm and Haas Company
④— A Trademark of BASF Wyandotte Corporation
⑤— A Trademark of Witco Chemical Corporation.
⑥— A product of Hodag Chemical Corporation.

All of the above listed solubilizing agents have been used in the process of this invention.

Many of the polyether solubilizing agents in the preceding list may be found in *McCutcheon's Publications — Combined Edition*, MC Publishing Company, Glen Rock, NJ, 1976. The synthesis of macrocyclic or crown ethers is found in Pederson, C. J. *J. Am. Chem. Soc.*, 89, 7017 (1967) and Belgian Patent 829,563.

For the purpose of this application, the following definitions will apply:

P—NO₂DPA = para-nitrodiphenylamine
SA = solublizing agent
Crude Yield = ((weight of product after work-up minus weight of SA)/(theoretical weight p-NO₂DPA at 100 percent conversion)) × 100.
True Yield = Crude Yield × (percent p-NO₂ DPA in product)/100.
Parts = parts by weight per 100 parts by weight PCNB.
ppm = parts per million or milligrams per liter.
PEG = polyethylene glycol.
RXn = reactions.

Referring to formula (X), solubilizing agents wherein $R_6$ is an alkoxyphenoxy moiety and $R_7$ is hydrogen are illustrated by compounds 7 through 14 of the above list. It is actually the long polyether or polyethylene oxide part cf the molecule which is postulated to be the active part of the molecule for solubilization.

Polyether solubilizing agents having the generic structure of formula (X) wherein $R_6$ is alkoxy, H, or hydroxy and $R_7$ is alkyl or hydrogen and represented by compounds numbers 1,2, 4–6, 25–31, and 36–40.

In the catalytic process, it is preferred to use either a polyethylene glycol (3,000–10,000 MW) or a methoxy terminate PEG (750–5,000 MW) at a charge level of 0.25 to 4 parts. The preferred catalysts in this system are cuprous salts (e.g. cuprous cyanide). The preferred reaction temperature is in a range of 185° to 205° C.

The order of addition of ingredients is limited as follows: if the catalyst is added at the same time as the solubilizing agent, they must be added when the reacting mixture is at reaction temperature (e.g. 185° C.). If the solubilizing agent is added at the beginning, before reaction temperature is reached, the catalyst must be added after the mixture has reached reaction temperature. If the catalyst is added at the beginning, before reaction temperature has been reached, the solubilizing agent must be added after the mixture has reached reaction temperature. Of the three methods, the latter two are preferred. It has been found that there is an interaction between the catalyst the SA, and the neutralizing agent at a temperature below reaction temperature which forms an unreactive complex.

The catalyst level should generally be from 0.9 to 1 part when $Cu_2(CN)_2$ is used.

The preferred work-up in the catalytic process using solubilizing agents is direct filtration of the hot reaction product without the water wash and azeotropic distillation steps previously described.

In the preferred mode of the formanilide process, the SA is a methoxy terminated PEG (750–5000 MW) or a PEG (300–7500 MW), charged at a level of 1–5 parts. Reaction temperature is 55° to 175° C.

It is also preferred to minimize the excess formanilide charged. This is possible because of the more efficient reaction brought about by the solubilizing agent. With reduced formanilide in excess at the end of the reaction, the work-up is simplified, and effluent COD is reduced.

The formanilide process with the inclusion of solubilizing agents is preferred to the catalytic process.

Certain crown ethers and alkyl or alkoxy terminated polyethylene glycols allow the use of sodium carbonate in the preparation of P-NO₂DPA, instead of $K_2CO_3$ as a neutralizing agent. There are advantages of cost and the elimination of potassium ions from the effluent stream which make sodium carbonate a preferable neutralizing agent.

A more detailed explanation of the process of this invention is furnished in the description of representative experiments utilizing the process. The several experimental procedures will first be described, and they will be followed by data tables showing experimental results utilizing the various solubilizing agents.

I — CATALYZED P-NO₂DPA IN GLASSWARE

Charge: 100 grams PCNB; 50 grams anhydrous $K_2CO_3$; 150 grams (total) aniline; 1 gram $Cu_2(CN)_2$; 100 mls. toluene (added at 185° C.). Any changes in the charge are indicated. The charge was made to a 1-liter, 3-neck flask, equipped with a dropping funnel, stirrer, thermometer, and an air condenser going up to a distillation head which lead down through a water condenser to a Dean-Start water trap and from the trap into a graduated cylinder. The contents of the 3-neck flask were heated with stirring to 185°-188° C. (about one hour heatup period). The SA was added at this temperature as a liquid through the dropping funnel or as a hot aniline solution requiring 10–20 grams aniline to dissolve the solids in the case of a solid SA.

The toluene was added through the dropping funnel at a rate of approximately 1 to 2 drops per second to maintain an overhead temperature of 105°–125° C. and a reaction temperature of 185°–190° C. The reaction was run as long as necessary to reduce the H₂O flow rate to the Dean-Stark trap down to about 0.1 ml./hour and to obtain about 6.25 to 6.75 ml. H₂O total. Toluene/aniline mixture collected in the graduated cylinder and was recycled back through dropping funnel, maintaining the aniline outside the reaction to a mini The above reaction was thereafter cooled to approximately 95° C., and 200 ml. of toluene was added. 180 ml. of water was then added, and the mixture was stirred approximately 1½ hours at about 85°–88° C. The aqueous layer was removed, and the organic layer remaining was heated with stirring so as to distill the azeotrope of toluene and water. The organic solution remaining was then filtered hot to remove the last traces of inorganic salts and the volatiles were stripped off at 185°–190° C. at approximately 10–20 mm. Hg. vacuum.

The heavies remaining were weighed to determine the crude-yield (136 grams theory). The hot stripped heavies were then poured into an evaporating dish and allowed to crystallize.

The crystallized product was crushed and analyzed by liquid and gas chromatography.

II — CATALYZED P-NO₂DPA IN BENCH SCALE EQUIPMENT

The reactions were run in an oil heated gallon reactor, equipped with a button drain, charge port and thermocouples located in the reactor and oil entering the jacket of the reactor. The reactor pot was stirred with a 3-inch turbine stirrer and driven with a variable speed motor. A 12-in. × 3-in. insulated column, equipped with a heat riser and bottom drain back to the reactor, packed with berl saddles, was connected to the top of the reactor. A thermocouple above the insulated packed column measured the overheads as they came through the column and another thermocouple was located about 2 inches down in the berl saddles near the top of the column.

The volatiles that came over when down through a water cooled condenser, into a 12-in. × 2-in. column equipped with a vent. The 12-in. × 2-in. column was added as a water trap and had a ⅜ inch tube coming up through the bottom and extended approximately 1½ inch up into the trap. The bottom of the trap had a drain so that water could be drained off into a graduated cylinder.

The ⅜ inch tube that came up through the bottom of the trap removed the aniline-toluene solution without pumping back the water.

The aniline-toluene solution was continuously pumped back to the top of the insulated column and some back to the reactor. The pumping was controlled with a variable stroke bellows pump. Retometers on the recycle to the top of the insulated column and to the reactor controlled and indicated the flow rates.

A typical run was as follows:

20 gms. aniline was charged to the reactor to fill the bottom drain.
945 gms. para-chloronitrobenzene (PCNB),
475 gms. anhydrous $K_2CO_3$,
950 gms. aniline,
100 ml. toluene was charged through the reactor port.

The agitator was turned on — 9.45 gms. $Cu_2(CN)_2$ was added with stirring. The preheated oil from the oil furnace was then pumped into the jacket of the reactor and after an approximate ¾–1 hour heat-up — a typical reaction with a rapid heat profile occurred as indicated. Such a rapid heat profile is preferred.

| Rxn Time Hrs. | Rxn Pot Temp. °C. | Insulated Column Temp. °C. | Overheads Temp. °C. | ml/min Recycle to OH* | ml/min Recycle to pot | ml H₂O Collected (Theory 54 ml) |
|---|---|---|---|---|---|---|
| 0 | 188 | 106 | 104 | — | — | 7 ml. |

SA, 1–2% based on weight of the PCNB - was blown into the reactor using N₂ pressure. Solid
SA's were first dissolved in aniline or toluene and charged as liquids.
0.166 hrs. 189° - Start recycling aniline-toluene solution.

| Rxn Time Hrs. | Rxn Pot Temp. °C. | Insulated Column Temp. °C. | Overheads Temp. °C. | ml/min Recycle to OH* | ml/min Recycle to pot | ml H₂O Collected (Theory 54 ml) |
|---|---|---|---|---|---|---|
| 0.25 | 186 | 115 | 124 | ~20–25 | — | 11 |
| 0.50 | 187 | 116 | 128 | " | — | 15 |
| 1.0 | 190 | 116 | 126 | " | — | 25 |
| 2.0 | 194 | 114 | 122 | " | — | 36 |
| 3.0 | 196 | 114 | 120 | " | — | 45 |
| 4.0 | 198 | 112 | 118 | " | ~2.0–2.5 | 53 |
| 5.0 | 200 | 114 | 116 | " | " | 57 |
| 6.0 | 202 | 112 | 114 | " | " | 59 |
| 7.0 | 203 | 112 | 113 | " | " | 60 |

-continued

| Rxn Time Hrs. | Rxn Pot Temp. °C. | Insulated Column Temp. °C. | Overheads Temp. °C. | ml/min Recycle to OH* | ml/min Recycle to pot | ml H₂O Collected (Theory 54 ml) |
|---|---|---|---|---|---|---|
| 7.5 | 201 | 112 | 114 | " | " | 60-¼ |

* = overheads insulated column.

The reactor was cooled to 120°–125° C. with the aid of an external water cooled condenser on the oil lines to the pot. The reaction product mixture was removed from the reactor through a preheated bottom drain.

1000 ml. toluene and 500 ml. aniline were used to rinse out the pot. The aniline-toluene solution was heated to 120°–125° C. in the pot with stirring for about one-half hour and this was added to the reaction product mixture.

2000 ml. of distilled H₂O was added to the above mixture with stirring and the mixture was heated to 90° C. for 1½ hours. After standing for 15 minutes, the water layer with the dissolved salts was drawn off. The water layer was a clear yellow solution and was easily separated from the organic solution. The last traces of water were azeotroped off by taking the organic solution temperature up to 125°–128° C. (with stirring).

The hot organic solution was filtered through a preheated filter (140°–150° C.) and stripped to 190° C. at 15 mm. Hg. vacuum. Approximately 1230–1250 gms. product was obtained vs. a theory of 1285 gms.

The product was analyzed using an LC chromotograph bonded column. The water layer containing the dissolved salts was analyzed for Cu, CN and aniline.

In some cases the reaction was worked up by just filtering off the inorganics, i.e. the hot reaction product mixture was filtered through a preheated filter (140°–150° C.). The inorganic cake was washed 3 times with 300–350 ml. of boiling toluene. The SA facilitated the filtering operation by helping to cut the tars off the inorganic salts. The resulting dried cake was a gray powdered solid.

III — FORMANILIDE PROCESS

The first three formanilide reaction processes listed in Table 6 which follows were run in laboratory glassware equipment as described in procedure I above. The three neck flask was charged with 78 grams (1.52 gram moles) of 90% formic acid and 140 grams (1.5 gram moles) of aniline, and the mixture was stirred. The temperature rose to about 65° C. The reaction mixture was stirred an extra 5 minutes, and 60 ml. of toluene was added.

The resulting mixture, containing formanilide, was distilled to remove the toluene/water azeotrope (about 38 ml. of H₂O).

The bottoms from this distillation was cooled to about 100° C., and 157 grams (1.0 gram moles) PCNB and 100 grams anhydrous K₂CO₃ were added. The SA was added at this point, and the reaction mixture was stirred and heated to 165° C. Toluene (100 ml.) was added through the dropping funnel to maintain the temperature in the pot at 165°–167° C., and the overheads temperature at 101°–108° C. Water was collected until the rate distilling over diminished to approximately 0.1 ml./hr.

The reaction was then cooled to about 100°–125° C., and 200 ml. of toluene was added. The excess formanilide was mostly destroyed by adding 200 ml. water with 30 grams NaOH solution to the reaction mixture at a temperature below 100° C. and maintaining a 90°–95° C. temperature for 1½ hours with stirring. The aqueous layer, after the hydrolysis reaction, was drawn off and the remaining unhydrolyzed formanilide was destroyed by adding a second wash of 200 ml. of H₂O and maintaining 85°–95° C. temperature with stirring for approximately 1 hour. This water layer was discarded, and the organic layer was azeotropically distilled to remove the last traces of water. The reaction solution was filtered hot to remove any traces of inorganic salts.

The volatiles were stripped off at a pot temperature of 180°–185° C. at approximately 10–20 mm. Hg. vacuum. The product remaining was weighed to determine the crude yield (217 grams theory) and was then poured into an evaporating dish while hot and allowed to crystallize.

The crystallized product was crushed and analyzed.

The 100 grams of K₂CO₃ used constitutes a high level of K₂CO₃ neutralizing agent. This compares with a 78.5 gram charge (with PCNB proportions being the same) used in the catalyzed process.

IV — MODIFIED FORMANILIDE PROCESS

Amounts charged were the same as in III above. However, the equipment arrangement and reaction process were changed as follows: The air condenser was removed, and the Dean-Stark water trap was fitted to a Y adapter on top one of the three necks of the reactor flask. The water condenser was fitted on top of the vertical section of the Dean-Stark water trap. This change was found desirable because in the formanilide process, there is almost no aniline refluxing as there is in the catalyzed process. The formanilide is much less volatile than aniline and does not reflux. Therefore, the air refluxing condenser is unnecessary.

In this new, simpler arrangement, the water/toluene azeotrope is condensed in the water condenser, and flows down into the Dean-Stark trap where the aqueous layer separates and settles to the bottom from which it may be withdrawn. The toluene layer overflows the side tube of the Dean-Stark trap returning to the reaction flask.

A reservoir of toluene is held in the dropping funnel on one of the other three necks of the reaction flask, and this reservoir serves as the means for controlling reaction temperature more closely than by procedure III. Heat is added through a heating tensile surrounding the reaction flask. Temperature may be lowered by adding toluene from the dropping funnel, and temperature may be raised by removing toluene through the stopcock in the Dean-Stark trap.

The tables which follow present representative data of experiments utilizing the procedures described above and various solubilizing agents. The number designation of the SA corresponds to the numbers on the list of SA's given previously.

Table 1

Polyethylene Glycols (—OH or —H Terminated) in Catalyzed [Cu₂(CN)₂] Para-Nitrodiphenylamine

| Run | SA | Parts SA | Hours Reaction Time | Process I True Yield (P-NO₂DPA) Averaged | WASTE WATER ANALYSIS | | |
|---|---|---|---|---|---|---|---|
| | | | | | mg COD liter | Cu+ppm | CN−ppm |
| 1 | None | 0 | 14 | 80.5 | 24,000 | 569 | 212 |
| 2 | #2 | 2 | 10 | 79.4 | 12,800 | 275 | 392 |
| 3 | #4 | 2 | 8.5 | 86.8 | 16,000 | 176 | 175 |
| 4 | #25 | 4 | 5 | 83.4 | * No Data Obtained | | |
| 5 | #26 | 4 | 3.5 | 87.6 | * No Data Obtained | | |
| 6 | #26 | 2 | 5 | 91.4 | * No Data Obtained | | |
| 7 | #26 | 1 | 6 | 91.7 | 14,000 | 438 | 381 |
| 8 | #27 | 1 | 5.75 | 92.4 | 18,000 | 156 | 124 |
| 9 | #28 | 1 | 5.5 | 91.5 | 12,000 | 305 | 134 |
| 10 | #29 | 1 | 6 | 91.3 | 12,000 | 180 | 90 |
| 11 | #31 | 1 | 5.5 | 89.1 | * No Data Obtained | | |
| 12 | #32 | 1 | 5.5 | 90.7 | * No Data Obtained | | |
| 13 | #33 | 1 | 6.5 | 90.8 | * No Data Obtained | | |

* The reactions were filtered hot and not H₂O washed.

Table 2

Polyethylene Glycols, alkyl or alkoxy terminated, in [Cu₂(CN)₂] Catalyzed

| Run | SA | Parts SA | Hours Reaction Time | Process I True Yield (P-NO₂DPA) | WASTE WATER ANALYSIS | | |
|---|---|---|---|---|---|---|---|
| | | | | | mg O₂ COD liter | Cu+ppm | CN−ppm |
| 1 | None | 0 | 14 | 80.5 | 24,000 | 569 | 212 |
| 2 | #5 | 2 | 6.5 | 90.1 | 16,000 | 256 | 219 |
| 3 | #36 | 1 | 7 | 89.0 | 15,000 | 291 | 242 |
| 4 | #39 | 2 | 5 | 86.2 | 14,200 | 225 | 187 |
| 5 | #40 | 0.5 | 7 | 89.9 | 10,000 | 119 | 90 |

All of the runs in Tables 1 and 2 using solubilizing agents resulted in markedly shorter reaction times and improved waste water quality, and all but one resulted in improved yield.

The results of the above table demonstrate the preferability of cuprous salts over cupric salts. Also demonstrated is the feasibility of using sodium carbonate (more economical than potassium carbonate) as a neutralizing agent.

Table 3

Polyethylene Glycols in Process I Using Various Copper Metal and Copper Salt Catalysts

| Run | SA | Parts SA | Catalyst | Parts Catalyst | Hours Reaction Time | Crude Yield |
|---|---|---|---|---|---|---|
| 1 | None | — | Cu dust | 4 | ~24 | 98.5 |
| 2 | None | — | Cu dust | 1 | ~34 | 97.8 |
| 3 | #27 | 10 | Cu dust | 5 | 5 | 100 |
| 4 | #27 | 4 | Cu dust | 2 | 6 | 97.1 |
| 5 | #27 | 2 | Cu dust | 1 | 10 | 96.3 |
| 6 | #39 | 2 | Cu dust | 1 | 7 | 100 |
| 7 | #27 | 2 | Cu dust | 1 | 8.5 | 99.3 |
| 8 | #27 | 4 | Cu₂I₂ | 2 | 7 | 99.3 |
| 9 | #27 | 4 | Cu₂Cl₂ | 2 | 5 | 94.9 |
| 10 | #27 | 4 | Cu₂S | 2 | 13 | 91.2 |
| 11 | #27 | 4 | CuS | 2 | Very Slow Reaction | |
| 12 | #27 | 4 | CuO | 4 | 7 | 100 |
| 13 | #27 | 4 | Cu₂O | 2 | 8 | 99.3 |
| 14 | #39 | 2 | CuCl₂ | 2 | Very Slow Reaction | |
| 15 | #39 | 2 | Cu(Acetate)₂ | 1 | 5.75 | 88.2 |
| 16 | #39 | 2 | CuSO₄(Anhydrous) | 1 | ~10 | 99.3 |
| 17* | #39 | 8 | Cu₂(CN)₂ | 1 | ~17 | 91.9 |

*Note: Na₂CO₃ used as neutralizing agent instead of K₂CO₃, in same molar concentration.

Table 4

Crown Ethers in Process I

| Run | SA | Parts SA | Neutral Agent | Hours Reaction Time | True Yield | WASTE WATER ANALYSIS | | |
|---|---|---|---|---|---|---|---|---|
| | | | | | | mg O₂ COD liter | Cu+ppm | CN-ppm |
| 1 | None | — | K₂CO₃ | 14 | 80.5 | 24,000 | 569 | 212 |
| 2 | #15 | 0.25 | K₂CO₃ | 6 | 84.2 | * No Data Obtained | | |
| 3 | #15 | 2.0 | Na₂CO₃ | ~12 | 70.5 | * No Data Obtained | | |
| 4 | #16 | 0.25 | K₂CO₃ | 7.75 | 80.0 | * No Data Obtained | | |
| 5 | #17 | 2.0 | Na₂CO₃ | 7.75 | 86.5 | 11,000 | 65 | 10 |

Table 4-continued

Crown Ethers in Process I

| Run | SA | Parts SA | Neutral Agent | Hours Reaction Time | True Yield | WASTE WATER ANALYSIS | | |
|---|---|---|---|---|---|---|---|---|
| | | | | | | mg O₂ COD liter | Cu+ppm | CN-ppm |
| 6 | #18 | 2.0 | Na₂CO₃ | 9.75 | 87.3 | 7,000 | 50 | 37 |

\* These runs filtered hot and not worked up with water.

The data in Table 4 indicate that crown ethers can be used with sodium carbonate neutralizing agent and that the yield obtained is still reasonable at reduced reaction times. The runs which were filtered hot would produce very little water pollution since no water wash aqueous phase would be produced and sent to waste water treatment. Those runs (5 and 6) in which the normal work-up was used still indicate a greatly reduced pollution level.

Table 5

Various Polyglycols in Processes I and II

| Run | SA | Parts SA | Hours Reaction Time | True Yield P-NO₂DPA | WASTE H₂O ANALYSIS | | |
|---|---|---|---|---|---|---|---|
| | | | | | mg O₂ COD liter | Cu+ppm | CN-ppm |
| 1 | None | 0 | 14 | 80.5 | 24,000 | 569 | 212 |
| 2* | #10 | 4 | 6 | 82.2 | ** 8,700 | 540 | 470 |
| 3* | #12 | 1 | 8.5 | 80.2 | 11,000 | 1060 | 763 |
| 4* | #12 | 2 | 7 | 81.5 | 14,000 | 809 | 488 |
| 5* | #11 | 1 | 7.5 | 82.3 | **16,200 | 967 | 675 |
| 6 | #20 | 2 | 5 | 81.1 | ***No Data Obtained | | |
| 7 | #22 | 4 | 10 | 81.2 | ***No Data Obtained | | |
| 8 | #23 | 4 | 9 | 85.3 | ***No Data Obtained | | |
| 9 | #21 | 4 | 5.75 | 79.8 | ***No Data Obtained | | |

*Process II, those without * were run in Process I.
**Calculated from % aniline in waste H₂O analysis.
***Reactions filtered hot and not worked up with H₂O.

Table 5 indicates that the polyglycol adducts when used as solubilizing agents also result in greatly reduced reaction times and lower levels of water pollution. The yields in most runs were equivalent to or greater than the control.

Table 6

Processes III and IV

| Run | SA | Parts SA | % Excess Formanilide | Hours Reaction Time | Crude Yield |
|---|---|---|---|---|---|
| 1 | None | 0 | 50 | 9 | 100 |
| 2 | #27 | 1 | 50 | 5 | 100 |
| 3 | #27 | 4 | 50 | 3.25 | 100 |
| 4 | None | 0 | 25 | 11 | 96.3 |
| 5 | None | 0 | 10 | 14 | 92.2 |
| 6 | None | 0 | 5 | 18 | 90.3 |
| 7 | #39 | 2 | 50 | 4 | 100 |
| 8 | #39 | 2 | 25 | 6 | 98.6 |
| 9 | #39 | 2 | 10 | 7.5 | 97.7 |
| 10 | #39 | 2 | 5 | 8.5 | 95.4 |

Runs 1, 2 and 3 were done by Process III, the rest by Process IV. The data in Table 6 show that the formanilide process with the solubilizing agents is capable of even shorter reaction time than the catalytic process.

While certain representative embodiments and details have been shown for the purpose of illustrating the invention, it will be apparent to those skilled in the art that various changes and modifications may be made therein without departing from the spirit or scope of the invention.

What is claimed is:

1. An improved process for synthesizing para-nitrodiphenylamines by the steps of reacting:
   (A) a para-halonitrobenzene having the following structural formula:

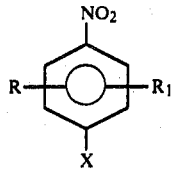

wherein R and R₁ are selected from the group consisting of hydrogen and alkyl radicals (1–9C) and X is chlorine or bromine;
   (B) with a nitrogen-containing aromatic compound selected from the group consisting of
      (1) primary aromatic amines having the following structural formula

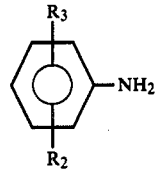

wherein R₂ and R₃ are selected from the group consisting of hydrogen, alkyl radicals containing from 1 to 9 carbon atoms (1–9C), alkoxy radicals (1–9C) and cycloalkyl radicals (5-6C); and
      (2) formanilides having the structural formula

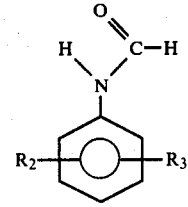

(C) in the presence of a neutralizing agent selected from the group consisting of alkali metal hydroxides, alkali metal salts, and oxides of alkali metals;

(D) with the proviso that when the nitrogen containing aromatic compound of part (B) is a primary aromatic amine the reaction is carried out in the presence of a copper catalyst selected from the group consisting of elemental copper and copper salts in a concentration of at least 0.1 parts by weight copper catalyst per 100 parts by weight of the para-halonitrobenzene;

(E) at a temperature of:
  (1) 170°–215° C. when the compound of part (B) is a primary aromatic amine; and
  (2) 120° to 195° C. when the compound of part (B) is a formanilide;

(F) at a pressure of from atmospheric pressure to 300 kPa; and (G) with an excess of the nitrogen-containing aromatic compound of part (B) over the stoichiometric amount of:
  (1) from 5 to 300% when the compound of part (B) is a primary aromatic amine; and
  (2) from 0 to 100% when the compound of part (B) is a formanilide; wherein the improvement comprises incorporating into the reacting mixture:
    (1) a solubilizing agent selected from the group consisting of:
      (a) macrocyclic ethers;
      (b) polyethers having as a major part of their structure the moiety $$+CHCH(CH_2)_{n_1}O+_{\overline{n_2}}$$
$$\phantom{+CH}|\phantom{CH(CH_2)}|$$
$$\phantom{+CHC}R_4\phantom{CH(C}R_5$$

wherein $R_4$ is selected from the group consisting of methyl and hydrogen, $R_5$ is selected from the group consisting of hydrogen and hydroxy, $n_1$ is 0 or 1, $n_2$ is equal to or greater than 1; and
      (c) compounds having structures selected from the structures of the macrocyclic ethers of (a) and the polyethers of (b) wherein the oxygen in the ether linkages has been replaced with a moiety selected from the group consisting of nitrogen and sulfur;
    (2) in a concentration of from 0.01 to 50 parts by weight of solubilizing agent per 100 parts by weight para-halonitrobenzene.

2. The improved process as recited in claim 1 wherein the nitrogen-containing aromatic compound of part (B) is selected from the group consisting of (1) aniline, and (2) formanilide.

3. The improved process as recited in claim 2 wherein the solubilizing agent is incorporated into the reacting mixture at a concentration of: (1) 0.25 to 4 parts when the nitrogen-containing aromatic compound is aniline and (2) 1 to 5 parts when the nitrogen-containing aromatic compound is formanilide.

4. The improved process as recited in claim 3 wherein the solubilizing agent is a macrocyclic ether selected from the group consiting of dibenzo-18-crown-6 ether, benzo-15-crown-5 ether, 18-crown-6 ether, and 15-crown-5 ether.

5. The improved process as recited in claim 3 wherein the solubilizing agent is a polyether selected from the group consisting of:
  (a) polyethers having the following structural formula $$R_6+CHCH(CH_2)_{n_1}O+_{\overline{n_2}}R_7$$
$$\phantom{R_6+CH}|\phantom{CH(CH_2)}|$$
$$\phantom{R_6+CHC}R_4\phantom{CH(C}R_5$$

wherein $R_6$ is selected from the group consisting of hydrogen, hydroxy, alkyl (1–30C), alkyloxy (1–30C), alkyl phenoxy (1–30C), phenoxy and acetoxy; and wherein $R_7$ is selected from the group consisting of hydrogen, alkyl (1–30C), alkyl phenyl (1–30C) and phenyl;
  (b) adducts of two or more polyethers having the formula of (a) above with each other;
  (c) adducts of one or more polyethers having the formula of (a) above wherein $R_5$ is hydrogen, either $R_6$ or $R_7$ is an hydroxy group, and $n_1$ is O with a compound selected from the group consisting of
    ($c_1$) aliphatic, benzyl, cycloaliphatic and alkenyl alcohols (1–30C); ($c_2$) aliphatic amines (1–30C); ($c_3$) aliphatic polyamines (1–30C, with the proviso that the amine and polyamine adducts are tertiaryamines); ($c_4$) salts of alkylarylsulfonates; and ($c_5$) salts of polyalkoxyalcohol esters of sulfosuccinic acid;
  (d) alkyl-amine guanidine polyoxyalcohols;
  (e) polyoxyalkyl esters of organic acids; and
  (f) branched polyethers with the repeating moiety $$+CHCH(CH_2)_{n_1}O+_{\overline{n_2}}$$
$$\phantom{+CH}|\phantom{CH(CH_2)}|$$
$$\phantom{+CHC}R_4\phantom{CH(C}R_5$$

and with end groups selected from the group consisting of $R_6$ and $R_7$.

6. The improved process as recited in claim 5 wherein the solubilizing agent is a polyether as described in Part (a) of claim 5.

7. The improved process as recited in claim 6 wherein the polyether is one in which $R_4$ and $R_5$ are hydrogen and $n_1$ is O.

8. The improved process as recited in claim 7 wherein the solubilizing agent is a polyether selected from the group consisting of polyethylene glycols and methoxy terminated polyethylene glycols.

9. The improved process as recited in claim 8 wherein the nitrogen containing aromatic compound is formanilide and wherein the solubilizing agent is selected from the group consisting of polyethylene glycol having a molecular weight of from about 3000 to about 7500 and methoxy terminated polyethylene glycol having a molecular weight of about 750 to about 5000.

10. The improved process as recited in claim 8 wherein the nitrogen containing a aromatic compound is aniline, the copper catalyst is a cuprous salt, the solubilizing agent is selected from the group consisting of polyethylene glycol having a molecular weight of about 3000 to about 10,000 and methoxy terminated polyethylene glycol having a molecular weight of about 750 to about 5000, and wherein the solubilizing agent is added to the reaction after reaction temperature has been reached.

11. The improved process as recited in claim 10 which further comprises removing inorganic salts from the reaction product at the end of the reaction by a physical unit operation selected from the group consisting of filtration and centrifugation.

* * * * *